United States Patent [19]

Mayambala-Mwanika et al.

[11] Patent Number: 4,587,220
[45] Date of Patent: May 6, 1986

[54] ASCORBATE INTERFERENCE-RESISTANT COMPOSITION, DEVICE AND METHOD FOR THE DETERMINATION OF PEROXIDATIVELY ACTIVE SUBSTANCES

[75] Inventors: Christine Mayambala-Mwanika, Mishawaka; Rodric H. White-Stevens, Middlebury, both of Ind.

[73] Assignee: Miles Laboratories, Inc., Elkhart, Ind.

[21] Appl. No.: 575,725

[22] Filed: Feb. 2, 1984

Related U.S. Application Data

[63] Continuation-in-part of Ser. No. 479,126, Mar. 28, 1983, abandoned.

[51] Int. Cl.$^4$ .......................... G01N 33/52; C12Q 1/28
[52] U.S. Cl. ......................................... 436/66; 422/56; 427/2; 435/28; 436/175; 436/904
[58] Field of Search ................... 422/56, 57; 436/66, 436/135, 904, 175; 435/14, 28, 805; 427/2

[56] References Cited

U.S. PATENT DOCUMENTS

| | | | |
|---|---|---|---|
| 3,104,209 | 9/1963 | Scott | 435/14 |
| 3,266,868 | 8/1966 | Harvill | 436/904 X |
| 3,411,887 | 11/1968 | Ku | |
| 4,168,205 | 9/1979 | Danninger et al. | 435/28 X |
| 4,288,541 | 9/1981 | Magers et al. | 435/28 X |
| 4,310,626 | 1/1982 | Burkhardt et al. | 435/28 |
| 4,314,030 | 2/1982 | Habich | |

FOREIGN PATENT DOCUMENTS

| | | |
|---|---|---|
| 844564 | 6/1970 | Canada |
| 55757 | 4/1983 | Japan |

OTHER PUBLICATIONS

Barteri et al., Chemical Abstracts, vol. 98, 1983, No. 98: 170042m.
Khan et al., Chemical Abstracts, vol. 68, 1968, No. 87477m.
Henry et al., "Clinical Chemistry-Principles and Techniques, 2nd Ed.", Harper & Row, 1974, pp. 1124–1125.
Kohn et al., J. Biol. Chem., 124, 163–168(1938).
Nielsen et al., Ugeskrift for Laeger, 141, 791–793, (1979).
Gifford et al., J. Amer. Med. Assoc., 178, 149–150 (1961).
O'Gorman et al., Brit. Med. J., 603–606, (1960).
Brandt et al., Amer. J. Clin. Pathol., 68, 592–594 (1977).
Bragagnolo, Chemical Abstracts, vol. 36, 1941, No. 1015.
Iwasaki, Journal of the Chemical Society of Japan, 63, 820–826 (1942).
Lohs, Chemical Abstracts, vol. 67, 1967, No. 120383z.
Khan et al., J. Amer. Chem. Soc., 89, 4176; 7104 (1967).
Khan et al., J. Amer. Chem. Soc., 90, 3386 (1968).
Grinstead, J. Amer. Chem. Soc., 82, 3464 (1960).
White-Stevens, Clin. Chem., 28/4, 578–588 (1982).

*Primary Examiner*—Arnold Turk
*Attorney, Agent, or Firm*—Mary G. Boguslaski

[57] ABSTRACT

A composition, test means (and device) and method for determining peroxidatively active substances in a test sample are disclosed. The composition, test means (and device) and method are rendered resistant to the adverse affects of ascorbate which may be present in the sample by the inclusion in the composition of a metal chelate which is polycarboxyalkylamine derivative having the formula:

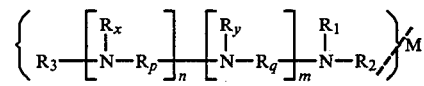

where:
(a) $R_1$ is hydrogen or straight or branched chain alkyl alcohol or alkyl carboxylic acid radicals having from 2 to 3 carbon atoms; $R_2$, $R_3$, $R_x$ and $R_y$, same or different, are straight or branched chain alkyl alcohol or alkyl carboxylic acid radicals having from 2 to 3 carbon atoms; where at least two of $R_1$, $R_2$, $R_3$, $R_x$ or $R_y$ are alkyl carboxylic acid radicals so defined;
(b) $R_p$ and $R_q$, same or different, are straight or branched chain alkylene radicals having from 1 to 3 carbon atoms or divalent 1,2-cycloaliphatic radicals having from 6 to 9 carbon atoms;
(c) n is an integer having a value of from 0 to 1; m is an integer having a value of from 0 to 2; where if m is greater than 0, repeated $R_p$ and repeated $R_q$ radicals may be the same or different; and
(d) M is $Fe^{+3}$.

The composition also comprises an organic hydroperoxide and an indicator capable of providing a detectable response in the presence of peroxide and the peroxidatively active substance. The test means comprises a carrier matrix incorporated with the composition, and the method comprises immersing the test means (or device) in the test sample and observing a color or other detectable response.

23 Claims, No Drawings

ASCORBATE INTERFERENCE-RESISTANT COMPOSITION, DEVICE AND METHOD FOR THE DETERMINATION OF PEROXIDATIVELY ACTIVE SUBSTANCES

This application is a continuation-in-part of U.S. Ser. No. 479,126, filed Mar. 28, 1983, and now abandoned.

BACKGROUND OF THE INVENTION

1. Field of the Invention

This invention relates generally to analytical determinations of peroxidatively active substances in test samples, and particularly to a composition, test means, device and method useful in such determinations and resistant to possible adverse effects from ascorbic acid which may also be present in the sample.

2. Background Art

Many analytical methods are presently available for detecting the presence of peroxidatively active substances in biological samples such as urine, fecal suspensions, and gastrointestinal contents. For example, hemoglobin and its derivatives, the analytes determined by conventional occult blood tests, are typical of peroxidatively active substances because they behave in a manner similar to the enzyme peroxidase; as such, they are also referred to as pseudoperoxidases. Peroxidatively active substances are enzyme-like by virtue of their catalysis of the redox reaction between peroxides or hydroperoxides and such indicator compounds as benzidine, o-tolidine, 3,3',5,5'-tetramethylbenzidine, 2,7-diaminofluorene and the like, producing a detectable response such as a color change. Hence, most methods for determining the presence of occult blood in test samples rely on this pseudoperoxidase activity.

A number of analytical methods for determining peroxidatively active substances have evolved which rely on the enzyme-like catalysis of the peroxidative oxidation of colorforming indicators. Primarily, these include wet chemistry or solution procedures and the so-called "dip-and-read" type, reagent-bearing strip devices. Of the former, a typical example is set forth in R. M. Henry, et al., *Clinical Chemistry Principles and Techniques*, 2nd ed., 1124–1125 (Hagerstown, Md.: Harper and Row, 1974). This exemplary procedure involves the use of glacial acetic acid (buffer), diphenylamine (indicator) and hydrogen peroxide. While such wet chemistry methods have proven analytical utility, they possess many disadvantages, two examples of which are poor reagent stability and inadequate sensitivity.

Another method for the determination of peroxidatively active substances, and one presently preferred by most clinical analysts, utilizes the so-called "dip-and-read" reagent strip device. Typical of such "dip-and-read" devices is one commercially available from the Ames Division of Miles Laboratories, Inc. under the trademark HEMASTIX ®. This device comprises a porous paper matrix impregnated with a buffered mixture of an organic hydroperoxide and an indicator, affixed to a plastic strip or handle. Upon immersion of the matrix in a liquid containing hemoglobin, myoglobin, erythrocytes or other peroxidatively active substances, i.e., pseudoperoxidases, a blue color develops in the matrix, the intensity of which is proportional to the concentration of the substance in the sample. By comparing the color developed in the matrix to a standard color chart, the analyst can determine, on a semiquantitative basis, the amount of analyte present in the sample.

Primarily, the advantages of such reagent strips over wet chemistry methods are: (1) the strip format is easier to use, requiring neither the preparation of reagents nor attendant apparatus; and (2) greater stability of reagents is afforded in the strip, resulting in improved accuracy, sensitivity and economy.

Whether a particular analysis for a peroxidatively active species is undertaken by either of the aforedescribed methods, a problem inherent to both exists: interference caused by the presence in the sample of reducing agents in general and ascorbic acid or ascorbate ion in particular (hereafter referred to as ascorbate interference). In the case of urinalysis for example, the recent popularity of diets which include high dosages of vitamin C (ascorbic acid) has resulted in serious ascorbate interference problems in analyzing for certain urine constituents, such as occult blood. Patients on such diets typically exhibit elevated levels of urinary ascorbate.

As early as 1938, the adverse effects of reducing agents such as ascorbate were recognized. R. Kohn and R. M. Watrous, *Journal of Biological Chemistry*, 124, 163–168 (1938). The same problem still plagues this area of diagnostic analysis, as evidenced by a proposal of 1979 that when an occult blood (a pseudoperoxidase) analysis is performed a simultaneous ascorbate analysis should also be performed in order to gauge the accuracy of the occult blood determination. L. Nielsen, P. J. Jorgensen and A. C. Hansen, *Ugeskrift for Laeger*, 141, 791–793 (1979).

Many attempts at removing ascorbate interference with test systems, such as systems containing glucose-sensitive reagents, are reported in the literature. With regard to glucose-sensitive assays, approaches have ranged from filtering out ascorbate before it reaches the reagents, to the utilization of an enzyme to decompose it, in situ.

Accordingly, Canadian Pat. No. 844,564 to Dahlqvist discloses a device for glucose determination in urine or other media which includes, in addition to a porous portion impregnated with normal glucose-responsive reagents, an additional portion to receive the urine test sample. The sample-receiving portion comprises an ion exchange material, whose singular function in the device is to adsorb any ascorbate present in the urine sample.

U.S. Pat. No. 4,168,205 to Danninger et al., suggests incorporating the enzyme ascorbate oxidase into the test reagent formulation; any ascorbate present in the sample will be enzymatically oxidized by the ascorbate oxidase to dehydroascorbate, a compound which does not adversely affect the desired analysis.

Another approach to alleviating ascorbate interference is reflected in Japanese Provisional Patent Publication No. 55757/1983 to Fuji Zoki Seiyaku K.K. The publication discloses the use of metal chelates of various ligands such as ethylenediaminetetracetic acid and diethylenetriaminepentacetic acid to pretreat a sample which will then be assayed for cholesterol, glucose or other components such as uric acid.

U.S. Pat. No. 3,411,887 to Ku describes the elimination of ascorbate interference with reagent systems which rely on enzymatic oxidizing substances such as glucose oxidase, by using an ascorbate "trapping system". The "trapping system" involves an ionizable heavy metal compound which when ionized has an oxidation-reduction potential falling between a redox indicator dye and ascorbate. Some suitable metals which are cited as examples include cobalt, iron, mercury and nickel.

U.S. Pat. No. 4,288,541 to Magers et al., commonly assigned herewith, describes the use of mercuric ion complexes, such as mercuric sarcosinate, to impart ascorbate resistance to a glucose/glucose oxidase assay system.

In addition to the foregoing, attention to the ascorbate problem with glucose tests is manifested by:
1. H. Gifford, et al., *J. Amer. Med. Assoc.*, 178, 149-150 (1961).
2. P. O'Gorman, et al., *Brit. Med. J.*, 603-606 (1960).
3. R. Brandt, et al., *Clin. Chem. Acta*, 51, 103-104 (1974).
4. R. Brandt, et al., *Am. J. Clin. Pathol.*, 68, 592-594 (1977).

Similar to the approach of the above-cited Ku patent, other literature deals with the complexing and oxidation of ascorbate using cobalt. For example, G. Bragagnolo, *Ann. Chim. Applicata*, 31, 350-368, 1941, reported that solutions of ascorbic acid were oxidized by air in the presence of cobalt metal. Also, similar activity has been reported for $Co(NH_3)_6Cl_3$ by Tomokichi Iwasaki in *Journal of the Chemical Society of Japan*, 63, 820-826 (1942).

Although the foregoing art deals extensively with analytical systems for glucose determinations, no suggestions are set forth as to resolution of the ascorbate interference problem in connection with the determination of such peroxidatively active substances as peroxidase and pseudoperoxidases such as occult blood (hemoglobin). Notwithstanding the disclosure of the Ku patent, supra, the aforementioned art indicates that metal ions, such as Co(III), are, in fact, also pseudoperoxidases. For example, Co(III) acetate is used commercially to catalytically decompose cumene hydroperoxide. [*The Merck Index*, 9th ed., 311 (1976).] A series of Co(III) complexes are reported to catalytically decompose peroxides by K. Lohs., *Monatsber. Deut. Akad. Wiss. Berlin*, 8, 657-659 (1966) (See *Chem. Abstracts*, 67, 120383z. 1967). One skilled in the art would clearly, therefore, be led to believe that the use of any such metal complexes in a typical analytical formulation for the determination of peroxidatively active substances, i.e., one containing an organic hydroperoxide and an indicator, would cause deleterious interaction with the hydroperoxide, either producing "false positive" results, or otherwise rendering it unreactive to the peroxidatively active substance of interest, such as occult blood, and thus useless for such determinations. In fact, efforts to use mercuric complexes, such as mercuric sarcosinate, in occult blood tests failed.

U.S. Pat. No. 4,310,626 to Burkhardt et al., commonly assigned herewith, addresses the foregoing problem in describing the use of ammonium Co(III) complexes for abating ascorbate interference with compositions for determining peroxidatively active substances. This patent discloses such compositions which comprise an organic hydroperoxide and a suitable indicator, such as 3,3'5,5'-tetramethylbenzidine, together with ammonium Co(III) complexes such as $Co(NH_3)_6Cl_3$, among others. These complexes, however did not impart sufficient ascorbate-resistance to an occult blood test to be commercially advantageous.

Other approaches to dealing with ascorbate interference in analytical determinations of peroxidatively active substances include, for example, West German Pat. No. 29 07 628. This German patent involves urinalysis in solution, whereby a urine sample is pretreated with one or more oxidants to remove ascorbate, and then contacted by the appropriate analytical reagents. The oxidants disclosed are sodium iodate, sodium periodate, calcium hydrochlorite, potassium triiodide, sodium hydrochlorite, chloroamine and bromosuccinimide.

In summary, various approaches to alleviating the interference problem presented by ascorbic acid in determinaton of peroxidatively active substances have included such techniques as the use of various Co(III) ammonium complexes, pretreatment of the sample with oxidizing agents and direct addition to the reagent composition of alkali metal iodates.

Pseudoperoxidases such as hemoglobin are often studied as alternate peroxidase systems in order to learn more about the mechanism of action of natural peroxidases such as those obtained from horseradish or potatoe sources. Ascorbic acid has long been known as a classical substrate for peroxidase, and ascorbic acid oxidation in the presence of metal chelates which act as pseudoperoxidases is a known phenomenon. In 1967 and 1968, M. Khan and A. Martell reported on kinetic studies of ascorbic acid oxidation in the presence of several ferric and cupric chelates over a pH range of 1.8 to 3.45. [Khan, M. and Martell, A., *J. Am. Chem. Soc.*, 89, 4176 (1967); *J. Am. Chem. Soc.*, 89, 7104 (1967); *J. Am. Chem. Soc.*, 90, 3386 (1968).] A variety of kinetic and thermodynamic parameters were investigated in these studies. The result was a rank order of effectiveness of different chelates according to their abilities to oxidize ascorbic acid. Of four aminopolycarboxylic acids studied by these writers, the N-(2-hydroxyethyl)ethylenediaminetriacetic acid (HEDTA) chelate of $Fe^{++}$ was found to be the fastest oxidant. Both the work of Martell, and an earlier study by Grinstead, regard this ascorbic acid oxidation activity to constitute a "model" peroxidase system. [Grinstead, R. R., *J. Am. Chem. Soc.*, 82, 3464 (1960).] Such studies as the foregoing by Grinstead constituted an attempt to study the peroxidase mechanism by means of a certain ferric chelate whose structure could mimic that of the iron-containing heme found at the active site of the enzyme peroxidase. Indeed, the writers use the phrase "model peroxidase system" repeatedly in their papers. However, because of the "model" peroxidase activity shown by this chelate and others which are similar in reactivity, one would certainly not expect that such substances could be incorporated into organic hydroperoxide/indicator systems such as those now typically used in analytical reagent compositions and devices for the determination of peroxidase or other peroxidatively active substances. Moreover, research studies undertaken by the assignee of the present invention in connection with peroxidase activity revealed that, with indicators such as 3,3',5,5'-tetramethylbenzidine (TMB) or o-tolidine (indicators which are typically used in analytical systems to determine the presence of peroxidatively active substances), such activity could be expected to occur some 200 times faster than with ascorbic acid. White-Stevens, R. H., *Clin. Chem.*, 28, 578 (1982). Accordingly, it can be assumed that if such peroxidatively active metal chelates, "model" peroxidases, act to so readily oxidize ascorbic acid—an assumption made by Khan, Martell and Grinstead—then the peroxidase reaction with such indicators as TMB would proceed at least at the same rate as with ascorbic acid, if not some 200 times faster (as suggested in these latter studies, which were undertaken on horseradish peroxidase). Clearly, if an extremely reactive analyte is incorporated into the very reagent formulation designed to change color in the presence of that analyte, it is to be expected that "false positive" results would be obtained.

SUMMARY OF THE INVENTION

The foregoing teachings and suggestions notwithstanding, it has now been discovered that certain peroxidatively active metal chelates, and in particular certain metal chelates of polycarboxyalkylamines, when used in the manner of the invention as described herein, not only fail to produce expected "false positive" results in a composition comprising a system of reagents for determining peroxidatively active substances, but actually are unexpectedly advantageous in such systems in terms of reliability, stability, and sensitivity of the system to an analyte being determined. Moreover, it has been found that use of the metal chelates according to the present invention is particularly advantageous in overcoming the inaccuracies which can be caused by interference from ascorbate ion present in a test sample.

Accordingly, the present invention is based upon this discovery, relates generally to analytical determinations of peroxidatively active substances which are resistant to ascorbate interference, and particularly to ones which according to the instant invention utilize a composition comprising an organic hydroperoxide and a redox indicator, for example, o-tolidine or 3,3',5,5'-tetramethylbenzidine, as well as a peroxidatively active metal chelate. In such determinations, the peroxidatively active analyte, because it mimics the enzyme peroxidase, catalyzes or otherwise participates in a reaction between the indicator and the organic hydroperoxide. The reaction yields a color or other detectable response, the intensity of which is indicative of the concentration of the analyte. Ascorbate ion, when present, causes a serious interference problem. The presence of a peroxidatively active metal chelate in the composition would also be expected to interfere with the analytical determination of a peroxidatively active analyte. Nevertheless, it has been discovered that novel compositions, test means (and devices), resistant to the interfering effects of ascorbic acid in a sample, can be successfully formulated for detecting the presence of a peroxidatively active substance in the sample; which compositions, test means (and devices) include metal chelates of polycarboxyalkylamine derivatives known also as "model peroxidases".

Accordingly, the composition of the invention comprises an organic hydroperoxide, an indicator capable of providing a detectable response, such as a color change, in the presence of the peroxidatively active substance and peroxide, and, additionally, a metal chelate which is a polycarboxyalkylamine derivative having the general formula

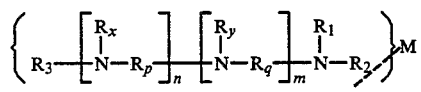

where $R_1$ is hydrogen or straight or branched chain alkyl alcohol or alkyl carboxylic acid radicals having from 2 to 3 carbon atoms; $R_2$, $R_3$, $R_x$ and $R_y$, same or different, are straight or branched chain alkyl alcohol or alkyl carboxylic acid radicals having from 2 to 3 carbon atoms; where at least two of $R_1$, $R_2$, $R_3$, $R_x$ or $R_y$ are alkyl carboxylic acid radicals so defined; $R_p$ and $R_q$, same or different, are straight or branched chain alkylene radicals having from 1 to 3 carbon atoms or divalent 1,2-cycloaliphatic radicals having from 6 to 9 carbon atoms; n is an integer having a value of from 0 to 1; m is an integer having a value of from 0 to 2; and M is $Fe^{+3}$.

Preferred compounds are those for which m is 0; n is 0 or 1 and $R_p$ is an ethylene radical. Particularly preferred are the metal chelates of polycarboxyalkylamine derivatives in which the alkyl carboxylic acid radicals are —$CH_2COOH$.

A preferred metal chelate is a ferric chelate of N-(2-hydroxyethyl)ethylenediaminetriacetic acid (Fe-HEDTA).

In a preferred embodiment of the invention, the composition is incorporated with a carrier matrix, for example, a bibulous paper, to form a test means which can be affixed to an inert support to form a test device. In addition, a method for making, and a method for using the test means (and device) are provided by the invention.

The inclusion of a metal chelate, according to the invention described herein, provides the compositions, test means (and devices) not only with excellent resistance to ascorbate interference, but also with unexpectedly advantageous stability, as reflected by experimental findings of good storage and elevated temperature stability and a lack of "false positive" results.

DETAILED DESCRIPTION OF THE INVENTION

Initial wet chemical experiments during development of the instant invention, and which employed only the ferric chelate of N-2(hydroxyethyl)ethylenediaminetriacetic acid (herein referred to as Fe-HEDTA; this notation is used for convenience only and is not meant to imply the existence of a covalent bond between the metal ion and the polycarboxyalkylamine derivative), ascorbic acid and buffer, confirmed the rapidity of ascorbic acid oxidation in the presence of this chelate, a result which would be expected from the previously-described reports of Khan and Martell. Thus, in view of how much faster TMB has been shown to be oxidized in peroxidase containing compositions, by comparison with ascorbic acid oxidation by such compositions, it was expected that a composition incorporating an organic hydroperoxide, an oxidizable indicator such as TMB and additionally, such a metal chelate, would be extremely unstable, quickly rendering "false positive" results.

However, upon further experimentation, the discovery was made that a composition can be formulated which includes such metal chelates, is suitable for the detection of peroxidatively active substance, and, moreover, is adaptable to a dry, solid state format, exhibiting good reagent stability during manufacture and in storage and a lack of "false positive" results when contacted with known hemoglobin-negative urine. This achievement of the present invention runs counter to any suggestion of the aforedescribed art which, as previously discussed, suggests that metal chelates such as Fe-HEDTA can be used as "model peroxidases", and thus would be unsuitable for use in a composition to determine the concentration of a peroxidatively active analyte.

Test means (and devices) for the detection of occult blood (OB), i.e., hemoglobin, in biological fluids such as urine, which have been produced from the novel composition of the invention, have been found to be resistant to abnormally elevated ascorbic acid levels in urine. As previously discussed, inhibition due to ascorbic acid is a serious problem, particularly in view of the fact that some 25% of urine specimens can be expected to exhibit ascorbic acid levels greater than 10 milligrams per deciliter (mg/dL). Conventional OB devices which do not include an ascorbate interference retardant of some type are usually found to be inhibited (i.e., rendered less sensitive to the presence of hemoglobin) by ascorbic acid concentrations as low as 5 mg/dL. However, devices produced in accordance with the present invention are greatly advantageous, in terms of ascorbate interference resistance, over such conventional devices, enabling the detection of peroxidatively active substances in fluids which contain relatively high levels of ascorbic acid, for example, on the order of 50 mg/dL.

The present invention thus provides compositions, test means (and devices) and methods for the determination of peroxidatively active substances in biological fluids such as urine. In addition to hemoglobin, other peroxidatively active substances can be detected by compositions, test means (and devices) of the invention, including, for example, peroxidase, myoglobin, erythrocytes, and other pseudoperoxidases. The invention involves the use of a metal chelate which is a derivative of an polycarboxyalkylamine and which is also recognized as a "model peroxidase", for the purpose of reducing or eliminating the deleterious effects of ascorbic acid on analytical assays performed on biological fluids. In this respect, the metal chelate functions to facilitate the oxidation of ascorbate ion which may be present in such fluids.

Compositions, test means (and devices) of the invention have been found to be substantially less susceptible to ascorbate interference, and to produce a response which is visually or instrumentally detectable, e.g., a color response, to the presence of trace hemoglobin levels on the order of 0.03 mg/dL, or even less.

The organic hydroperoxide contemplated for use in the composition of the invention can be selected from many well known organic hydroperoxides. One selected must, however, be capable of interacting with a peroxidatively active substance in the presence of an indicator to produce a detectable response, such as a color change or a change in the amount of light absorbed or reflected by the test composition. Among hydroperoxides which are particularly suitable are cumene hydroperoxide, t-butyl hydroperoxide, diisopropylbenzene hydroperoxide, 2,5-dimethylhexane-2,5-dihydroperoxide, paramenthane hydroperoxide, and other well-known hydroperoxides which are suitable for oxidizing the indicator used, or mixtures of these compounds. Of the foregoing, cumene hydroperoxide is most preferred.

Many indicators are suitable for use in the composition of the invention, so long as they are capable of interaction to produce a detectable response in the presence of an organic hydroperoxide and a peroxidatively active substance. These include, for example, the so-called "benzidine-type" compounds; benzidine; o-tolidine; 3,3',5,5'-tetra(lower alkyl)benzidine; 2,7-diaminofluorene; and mixtures of these or various others. The term "lower alkyl", as used herein, refers to an alkyl radical having from 1 to 6 carbon atoms, including methyl, ethyl, n-propyl and isopropyl, and the various butyl, pentyl and hexyl isomers. The indicator, 3,3',5,5'-tetramethylbenzidine (TMB), is especially preferred.

The suitability of a particular metal chelate selected for use is governed not only by its ability to facilitate the oxidization of ascorbic acid, but also by its compatibility with the other constituents of the composition. Thus, such suitable chelates have been found to include metal chelates of polycarboxyalkylamine derivatives which are represented by the general formula:

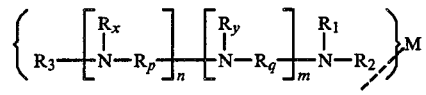

Accordingly, exemplary metal chelates which have been found suitable for use in the instant invention include the ferric chelates of N-(2-hydroxyethyl)-ethylenediaminetriacetic acid (Fe-HEDTA), ethylenediaminetetraacetic acid (Fe-EDTA), cyclohexylenediaminetetraacetic acid (Fe-CDTA), nitrilotriacetic acid (Fe-NTA), iminodiacetic acid (Fe-IMDA), ethylenediaminediacetic dipropionic acid (Fe-EDDP) both α and β forms), and hydroxyethyliminodiacetic acid (Fe-HIMDA) and mixtures thereof. The ferric chelate forms are generally preferred; most preferred are the compounds Fe-HEDTA and Fe-EDTA, most desirable is Fe-HEDTA. However, many suitable chelates are within the scope of the present invention in addition to those specifically set forth herein, as will be apparent to one of reasonable skill in the art, given the present teachings.

Accordingly, it has been found experimentally that Fe-HEDTA and Fe-EDTA, and particularly Fe-HEDTA, provide excellent results in compositions, test means (and devices) of the invention, most satisfactorily providing ascorbic acid interference resistance in occult blood tests (enabling the detection of hemoglobin), while providing good reagent stability prior to use and a lack of "false positive" results. Moreover, other metal chelate compounds herein specified, as well as many others, will perform satisfactorily. However, substantial variations in the rate at which a peroxidatively active substance can be detected when such other compounds are used, can be expected because of varying rates of ascorbate oxidation. Thus, it is to be understood that suitable metal chelates for use in the instant invention can be selected from any which are polycarboxyalkylamines derivatives within the class of compounds previously described, and that all such compounds can be expected to satisfactorily enable oxidation of ascorbate, placing them within the scope of the present invention. However, many in this regard will perform slowly and thus are less practical for commercial use and not preferred.

Suitable metal chelates for use in the present invention can be prepared by conventional laboratory procedures using polycarboxyalkylamine derivatives which are commercially available from Aldrich Chemical Co., Sigma Chemical Company or similar suppliers. For example the metal chelate, Fe-HEDTA, can be prepared by mixing equimolar amounts of commercially available HEDTA and $FeCl_3 \cdot 6H_2O$, in aqueous solution, to produce a 1:1 (mole:mole) Fe-HEDTA solution of iron:chelate. Other solution concentration ratios of metal:chelate can be easily prepared merely by varying the respective concentrations of the mixed solutions. It has been found that best results in terms of overcoming ascorbate interference are obtained when the concentration of metal ion to polycarboxyalkylamine derivative in the chelate is approximately a 1:1 (mole:mole) relationship.

A preferred range of concentration of a given metal chelate in different embodiments of the invention will vary widely. For example, in the case of Fe-HEDTA, a preferred concentration range presently is from about 0.5 millimolar (mM) to about 50 mM when used in a composition containing an organic hydroperoxide and a tetra(lower alkyl)benzidine indicator; this range has been determined to be optimum for resistance up to about a 50 mg/dL ascorbate concentration level in urine samples. Moreover, in experimental trials, lower concentrations of some suitable ferric chelates enabled comparatively rapid hemoglobin detection, whereas higher concentrations of the same chelates, or of other chelates, were less effective. These apparently anomolous results are more fully set forth, infra, and demonstrate the lack of a general correlation between chelate concentration and functionality or suitability in the composition of the invention.

It has been found experimentally that the majority of suitable metal chelates performing satisfactorily in the composition of the invention structurally possess an alkyl amine, or an amine central group, and also the carboxylic acid radical, —CH$_2$COOH. However, other chelates not having such characteristics, but which are within the general scope of compounds previously set forth, can be generally effective to overcome ascorbate interference and provide satisfactory sensitivity and stability, and are therefore, satisfactory for use.

It is to be appreciated that, in use, the performance of a particular embodiment of a composition, test means (and device) based upon the general concepts of the invention depends on many different factors. Since a typical urine specimen from a human subject accustomed to ingesting large quantities of ascorbic acid (Vitamin C) often contains from 25 to 100 or more mg/dL of ascorbate; a reference ascorbate level for research purposes has been selected to be approximately 50 mg/dL. Preferred embodiments of the ascorbate resistant composition, test means (and device) and method of the invention have been found to enable the detection of peroxidatively active substances in such specimens not only at the reference level of about 50 mg/dL, but also at various other ascorbate levels. In most cases, a prolonged response time may occur with ascorbate levels much greater than the chelate concentration level. As set forth, infra, "lag times", i.e., the time until an observable response occurs, have been found experimentally to range from less than ½ minute to about ½ hour, for preferred embodiments of the invention of differing chelate concentration levels which were tested for ability to detect hemoglobin in urine in the presence of a level of 50 mg/dL ascorbate.

In a preferred embodiment, the composition of the invention is used to produce test means (and devices) for the determination of a peroxidatively active substance. In such preferred embodiment, the composition can be incorporated with a suitable carrier matrix to form a test means. The carrier matrix can take on many forms, such as those disclosed in U.S. Pat. No. 3,846,247 (felt, porous ceramic strips, and woven or matted glass fibers). Also suitable are the matrices described in U.S. Pat. No. 3,552,928 (wood sticks, cloth, sponge material and argillaceous substances). The use of synthetic resin fleeces and glass fiber felts as carrier matrices is suggested in British Pat. No. 1,369,139; another British Pat. No. 1,349,623, proposes the use of light-permeable meshwork of thin filaments as a cover for an underlying paper matrix. Polyamide fibers are disclosed in French Pat. No. 2,170,397. Such disclosures notwithstanding, the materials conventionally used as carrier matrices, and which are especially preferred and suitable for use in the present invention, are bibulous materials such as filter paper and the like. It is to be appreciated, however, that the carrier matrix can appear in various physical forms as summarized above, as well as others, and that all such forms are suitable and intended for use in the present invention.

In the preparation of the test means of the invention, the constituents of the composition can be incorporated with the carrier matrix in a variety of ways. For example, the constituents can be dissolved or suspended in water or another suitable solvent, preferably an organic one such as ethanol, acetone or dimethylformamide (DMF), as well as mixtures of these solvents and of others. The solution or suspension can then be used to impregnate bibulous filter paper, as in the form of an ink wherein the reagents are printed on a suitable matrix; alternatively, the carrier matrix can be immersed in or coated with the composition, such as with a doctor blade.

The presently preferred method of incorporation of the constituents of the composition with the carrier matrix is to impregnate bibulous filter paper with two or more solutions or suspensions of the constituents. Impregnation thus is accomplished by dipping a piece of filter paper two or more times into such solutions or suspensions and drying the dipped paper in an oven after each dip. The test means thus formed is then laminated to one side of a piece of double faced adhesive tape, the laminate is slit into strips and each strip attached to an elongated sheet of plastic backing material (such as polystyrene) which is then slit parallel to its short dimension to form oblong devices with the impregnated paper at one end, the other end serving as a handle. The test device thus formed consists of a piece of the doubly dried and impregnated test means affixed, at one end, to one flat side of an elongated plastic support which then forms a convenient handle.

One preferred method for making the test means of the invention is wherein, for example, Fe-HEDTA is introduced into the filter paper along with the organic hydroperoxide but prior to addition of the indicator, in an aqueous first dip. Thus, the filter paper can be first impregnated with an aqueous solution of Fe-HEDTA and the hydroperoxide, along with one or more suitable solvents and/or buffers, e.g., triethanolamine borate and Tris(hydroxymethyl)amino methane-malonate (referred to herein as TRIS-malonate), dried, reimpregnated in a second dip solution of the indicator in a suitable solvent, for example, ethanol, and dried a second time. Such a "two-dip" process, where the metal chelate is first impregnated into the paper before the other active reagents, has been found to yield a test device exhibiting excellent ascorbate resistance and storage stability.

An especially preferred method for formulating the test means of the invention is to introduce the metal chelate and the reagents, except for the indicator, into the filter paper by immersing it in a first solution of the reagents as previously described, and thereafter drying the paper and subsequently adding the indicator via immersion of the dried paper into a solution of the indicator and a thickening agent, such as polyvinylpyrrolidone, in a suitable solvent, followed by a second drying.

In addition to the previously described test composition reagents and other ingredients, other components, such as various thickening agents, wetting agents, buffers, emulsifying agents and well known adjuvants can also be included in the composition, test means (and device) of the present invention. Thus, for example, as thickening agents, there can be used various materials in addition to or in place of polyvinylpyrrolidone, such as gelatin, algin, carrageenin, casein, albumin, methyl cellulose and the like. As wetting agents, it is preferable to use sodium dodecyl sulfate but any long chain organic sulfate or sulfonate, such as dioctyl sodium sulfosuccinate or sodium dodecylbenzene sulphonate can also be used. For the buffering systems, in addition to triethanolamine borate and TRIS-malonate, tartarate, phosphate, phthalate, citrate, acetate, succinate or other buffers can be employed. Preferably, the compositions are buffered to a pH value of from about 6.0 to 7.0. As emulsifying agents, polyvinyl alcohol, gum arabic, carboxy vinyl polymers and the like can be used. The organic solvents which are useful to suspend the indicator include most nonreactive, organic volatile solvents such as ethanol, acetone, DMF, chloroform, ethylene dichloride, benzene, ethyl acetate and the like. Of course the choice of other suitable solvents is within the ability of one skilled in the art given the present disclosure.

In use, the test means (or test device) can be immersed in the fluid or liquid suspension of the material to be tested and immediately withdrawn; or the sample, in liquid, solid or semi-solid form, can be applied to the test means (or device). In the presence of a peroxidatively active substance in the sample, the test composition produces a color change or other detectable response. If the response is color, it can be compared with precalibrated color standards for an estimation of the quantitative amount of peroxidatively active substance contained in the sample. Intact peroxidatively active substances, such as intact red blood cells, can appear as dots or flecks of color on the otherwise uncolored matrix. Hemolyzed peroxidatively active substances can uniformly color the matrix. In addition to visual comparison, various instrumental methods can also be employed to determine the quality of the color or other response developed, thus increasing the accuracy of the test by obviating the subjective determination of the human eye.

The following Examples are provided only in order to illustrate the concepts and advantages of the presently disclosed invention, and are not to be construed as imposing limitations upon the scope thereof. Any such limitations are intended to be defined solely by the claims appended hereto.

EXAMPLES

A. THE TEST COMPOSITION

EXAMPLE I—Fe-HEDTA

An experiment was conducted wherein the composition of the present invention, capable of determining the presence of peroxidase or another peroxidatively active substance in a test sample, and in particular hemoglobin, was prepared. The composition included, as an ascorbate interference retardant, a 1:1 (mole to mole indicated as M:M herein) ferric chelate of N-(2-hydroxyethyl)ethylenediaminetriacetic acid (Fe-HEDTA). The Fe-HEDTA chelate was prepared by dissolving 0.278 gram (g) of HEDTA in 100 milliliters (mL) of distilled water to produce a 10 millimolar (mM) HEDTA solution, and then dissolving 0.270 g of $FeCl_3.6H_2O$ into the 10 mM HEDTA solution. Ascorbic acid, at a concentration of 5 mM, was added to the composition in an amount sufficient to produce a 50 micromolar concentration level in the final volume of the solution. The constituents of the composition and the ascorbic acid were combined in the order and in the amounts listed in the following table. The final composition solution contained a 100 micromolar ($\mu M$) concentration of Fe-HEDTA, a concentration level, like the level of the other ingredients present, substantially less than would be used in a similar composition of the invention for incorporation into a solid state test means or device.

| | | |
|---|---|---|
| 0.2 Molar (M) sodium citrate buffer | | 9.5 mL |
| 10 mM Fe—HEDTA | | 0.1 mL |
| 10 g/dL* sodium dodecyl sulfate | | 0.1 mL |
| 1 M cumene hydroperoxide | | 0.1 mL |
| 10 mM 3,3',5,5'-tetramethylbenzidine | | 0.1 mL |
| 5 mM ascorbic acid | | 0.1 mL |

*grams per deciliter

The composition of the invention so produced was observed to form a blue color when an aqueous blood aliquot was added to produce a final concentration of 0.139 milligram of hemoglobin per deciliter in the solution, indicating the ability of the composition to detect the hemoglobin present despite the 50 $\mu M$ ascorbate level of the sample.

EXAMPLE II—Fe-EDTA

The experiment of Example I was repeated except that 10 mM of the ferric chelate of ethylenediaminetetraacetic acid (Fe-EDTA) solution was used, rather than Fe-HEDTA. The Fe-EDTA was prepared substantially as described in Example I, by dissolving 0.292 g of EDTA in 100 mL of distilled water and adding $FeCl_3.6H_2O$, as described in Example I. The composition so produced formed a blue color, as in Example I, in the presence of 0.139 milligram of hemoglobin per deciliter and 50 $\mu M$ ascorbate.

EXAMPLE III—Fe-CDTA

The experiment of Example I was repeated except that 10 mM of the ferric chelate of cyclohexylenediaminetetraacetic acid (Fe-CDTA) solution was used, rather than Fe-HEDTA. The Fe-CDTA solution was prepared by dissolving 0.346 g of CDTA in 100 mL of distilled water and adding $FeCl_3.6H_2O$, as described in Example I. The composition so produced formed a blue color, as in Example I, in the presence of 0.139 milligram of hemoglobin per deciliter and 50 $\mu M$ ascorbate.

EXAMPLE IV—Fe-IMDA

The experiment of Example I was repeated except that 10 mM of the ferric chelate of iminodiacetic acid (Fe-IMDA) solution was used, rather than Fe-HEDTA. The Fe-IMDA solution was prepared by dissolving 0.133 g of IMDA in 100 mL of distilled water and adding $FeCl_3.6H_2O$, as described in Example I. The composition so produced formed a blue color, as in Example I, in the presence of 0.139 milligram of hemoglobin per deciliter and 50 $\mu M$ ascorbate.

EXAMPLE V—Fe-NTA

The experiment of Example I was repeated except that 10 mM of the ferric chelate of nitrilotriacetic acid (Fe-NTA) solution was used, rather than Fe-HEDTA. The Fe-NTA solution was prepared by dissolving 0.191 g of NTA in 100 mL of distilled water and adding $FeCl_3.6H_2O$, as described in Example I. The composition so produced formed a blue color, as in Example I, in the presence of 0.139 milligram of hemoglobin per deciliter and 50 $\mu$M ascorbate.

EXAMPLE VI—Fe-EDDP$_\alpha$

The experiment of Example I was repeated except that 10 mM of the ferric chelate of $\alpha$-ethylenediaminediacetic dipropionic acid (Fe-EDDP$_\alpha$) solution was used, rather than Fe-HEDTA. The Fe-EDDP$_\alpha$ solution was prepared by dissolving 0.320 g of EDDP$_\alpha$ in 100 mL of distilled water, and adding $FeCl_3.6H_2O$, as described in Example I. The composition so produced formed a blue color, as in Example I, in the presence of 0.139 milligram of hemoglobin per deciliter and 50 $\mu$M ascorbate.

EXAMPLE VII—Fe-EDDP$_\beta$

The experiment of Example I was repeated except that 10 mM of the ferric chelate of $\beta$-ethylenediaminediacetic dipropionic acid (Fe-EDDP$_\beta$) solution was used, rather than Fe-HEDTA. The Fe-EDDP$_\beta$ solution was prepared by dissolving 0.320 g of EDDP$_\beta$ in 100 mL of distilled water, and adding $FeCl_3.6H_2O$, as described in Example I. The composition so produced formed a blue color, as in Example I, in the presence of 0.139 milligram of hemoglobin per deciliter and 50 $\mu$M ascorbate.

EXAMPLE VIII—Fe-HIMDA

The experiment of Example I was repeated except that 10 mM of the ferric chelate of hydroxyethyliminodiacetic acid (Fe-HIMDA) solution was used, rather than Fe-HEDTA. The Fe-HIMDA solution was prepared by dissolving 0.177 g of HIMDA in 100 mL of distilled water, and adding $FeCl_3.6H_2O$, as described in Example I. The composition so produced formed a blue color, as in Example I, in the presence of 0.139 milligram of hemoglobin per deciliter and 50 $\mu$M ascorbate.

EXAMPLES IX–XVI

Experiments were conducted substantially as described in Examples I–VIII, supra, to produce compositions according to the invention, except that in each case 9.4 mL of 0.2M sodium citrate buffer was used rather than 9.5 mL, and 0.2 mL of each ferric chelate was used, rather than 0.1 mL. This enabled a 200 $\mu$M concentration level of the ferric chelate to be present in each composition. In each case, the composition containing 200 $\mu$M ferric chelate, when tested as previously described, were observed to form blue colors in the presence of 0.139 milligram of hemoglobin per deciliter and 50 $\mu$M ascorbate, indicating an ability to detect the hemoglobin despite the presence of ascorbate in the sample. However, differences were noted between the times required for color to form, by comparison with the color formation times observed when the 100 $\mu$M ferric chelate compositions of Examples I through VIII were similarly tested. The color formation times in each case, referred to as "lag times", are set forth in the following table, and show that, as previously described, there appears to be no general relationship or correlation between the concentration of metal chelate, e.g., one of the foregoing ferric complexes, which is used in a composition of the invention and the ability of the composition to withstand ascorbate interference and allow the detection of a peroxidatively active substance.

| | | EXPERIMENTAL RESULTS: Color Formation, Lag Time (50 $\mu$M ascorbate) | |
|---|---|---|---|
| | | METAL CHELATE CONCENTRATION | |
| EXAMPLE NOS. | METAL CHELATE: 1:1 (M:M) $Fe^{3+}$—Chelate | 100 $\mu$M EXAMPLES I-VIII | 200 $\mu$M EXAMPLES IX-XVI |
| I and IX | $Fe^{3+}$—HEDTA | 18 sec | not done |
| II and X | $Fe^{3+}$—EDTA | 67 sec | not done |
| III and XI | $Fe^{3+}$—CDTA | 3 min | 2½ min |
| IV and XII | $Fe^{3+}$—IMDA | 5 min | 7 min |
| V and XIII | $Fe^{3+}$—NTA | 15 min | 5 min |
| VI and XIV | $Fe^{3+}$—EDDP$_\alpha$ | 18 min | 10 min |
| VII and XV | $Fe^{3+}$—EDDP$_\beta$ | 31 min | 19 min |
| VIII and XVI | $Fe^{3+}$—HIMDA | 20 min | 20 min |

B. THE TEST DEVICE

EXAMPLE XVII

An experiment was conducted wherein a solid state test device was prepared in accordance with the instant invention. The device comprised a paper carrier matrix incorporated with the composition of the invention as described in Example I, supra, except that the concentrations of the ingredients were varied to suit the solid state device format. Incorporation of the matrix with the composition and formation of the test device were carried out using the following procedures.

A 50 mM, 1:1 (mole:mole) ferric chelate of N-(2-hydroxyethyl)ethylenediaminetriacetic acid (Fe-HEDTA) was prepared by dissolving, in 100 mL of distilled water, 1.39 g N-(2-hydroxyethyl)ethylenediaminetriacetic acid, and then adding to the solution 1.35 g of $FeCl_3.6H_2O$.

Two solutions (composition follows) were prepared. To produce the test means, a piece of Whatman 3 MM filter paper having approximate dimensions of 6 inches by 4 inches was then impregnated with the reagent solutions, so that the paper became fully incorporated with the reagent composition after the second dip. The procedure used involved impregnating the paper by immersing it in the first solution, drying the impregnated paper, and subsequently further impregnating the dried paper by immersion in the second solution followed by a final drying. Drying was accomplished in a forced draft oven at 105° C. for about 8 minutes after the first impregnation, and at 50° C. for about 5 minutes following the second impregnation.

The first reagent solution was prepared by mixing the following ingredients:

| | |
|---|---|
| Distilled water | 74.0 mL |
| 1 M TRIS-malonate buffer, pH 6.5 | 10.0 mL |
| 5.5 M cumene hydroperoxide | 4.0 mL |
| 10 g/dL sodium dodecyl sulfate | 2.0 mL |
| 50 mM Fe—HEDTA (prepared as previously described | 10.0 mL |

The second reagent solution was prepared by mixing the following ingredients:

| | |
|---|---|
| Ethanol | 79.4 mL |
| 6-methoxyquinoline, free base form | 0.6 mL |
| 20% (w/v) polyvinylpyrrolidone (aqueous) (molecular wt. 40,000) | 20.0 mL |
| 3,3',5,5'-tetramethylbenzidine | 0.6 g |

The dried, impregnated paper was laminated to one side of a piece of double-sided adhesive transfer tape, commercially available from 3M Company, St. Paul, Minn. 55144. The laminate was then slit into portions measuring about 6 inches by 0.2 inches. One of these was attached, via the unused adhesive side, to a polystyrene sheet measuring about 3.5 inches by 6 inches and the resulting laminate was slit parallel to its short dimension to form test devices comprising a 3.5 inch oblong polystyrene strip carrying a square of the impregnated paper at one end, the other end serving as a handle.

Testing of devices produced according to the procedure of Example XVII, in urine samples which contained various concentration levels of hemoglobin and a 50 mg/dL concentration of ascorbate, yielded easily discernible blue color levels corresponding to the various hemoglobin levels, indicating the ability of the device to detect the hemoglobin present despite the high ascorbate levels of the samples.

EXAMPLE XVIII

The experiment of Example XVII was repeated, except that 10.0 mL of a 50 mM Fe-EDTA solution were used in the first reagent solution, in place of Fe-HEDTA.

Testing of devices, produced in accordance with Example XVIII, was carried out as previously described in urine samples containing various concentration levels of hemoglobin and 50 mg/dL ascorbate, and yielded easily discernible blue color levels corresponding to the various hemoglobin levels.

EXAMPLE XIX

The experiment of Example XVII was repeated, except that 10.0 mL of a 50 mM Fe-CDTA solution were used in the first reagent solution, in place of Fe-HEDTA.

Testing of devices, produced in accordance with Example XIX, was carried out as previously described in urine samples containing various concentration levels of hemoglobin and 50 mg/dL ascorbate, and yielded easily discernible blue color levels corresponding to the various hemoglobin levels.

EXAMPLE XX

The experiment of Example XVII was repeated, except that 10.0 mL of a 50 mM Fe-IMDA solution was used in the first reagent solution, in place of Fe-HEDTA.

Testing of devices, produced in accordance with Example XX, was carried out as previously described in urine samples containing various concentration levels of hemoglobin and 50 mg/dL ascorbate, and yielded easily discernible blue color levels corresponding to the various hemoglobin levels.

EXAMPLE XXI

The experiment of Example XVII was repeated, except that 10.0 mL of a 50 mM Fe-NTA solution was used in the first reagent solution, in place of Fe-HEDTA.

Testing of devices, produced in accordance with Example XXI, was carried out as previously described in urine samples containing various concentration levels of hemoglobin and 50 mg/dL ascorbate, and yielded easily discernible blue color levels corresponding to the various hemoglobin levels.

C. TEST DEVICE ASCORBATE INTERFERENCE RESISTANCE AND STABILITY

Further experiments were conducted to assess the ability of test devices, prepared as described in Example XVII, supra, to detect hemoglobin in urine in the presence of ascorbate after stress designed to mimic long storage. The experiments were conducted on some of the devices immediately after they had been freshly prepared, as well as on others after they had been stored for extended periods under elevated temperature conditions. In particular, the devices were tested and compared for performance immediately after preparation at ambient temperature (about 23° C.), and after ten (10) and twenty-eight (28) days of "heat stress" at about 50° C. in an oven.

A set of test urine solutions was formulated which contained various levels of hemoglobin. Two hemoglobin solutions were also prepared which contained ascorbate at a concentration level of 50 mg/dL.

A stock solution was prepared containing 15.4 mg/dL of hemoglobin, by diluting whole blood, with distilled water to a concentration of 15.4 mg hemoglobin per 100 mL water. The hemoglobin content of the whole blood had been previously determined by conventional techniques. A sample of pooled urine, previously screened to be negative in hemoglobin and ascorbic acid, was set aside as a blank. The test solutions were then prepared by pipetting aliquots of the blood solution into the pooled urine to form urine solutions containing 0.015, 0.031, 0.062 and 0.139 mg/dL hemoglobin. Part of the urine solutions having 0.031 and 0.062 mg/dL hemoglobin were isolated in separate containers, and ascorbic acid was added thereto to bring the solutions to a level of 50 mg/dL ascorbate immediately prior to the testing.

A set of devices, prepared as in Example XVII, as well as a control set of devices prepared as described in that Example with the exception that they included no Fe-HEDTA, were tested in the blank and in each of the hemoglobin/urine solutions. The devices were momentarily immersed in each solution, then removed and color formation in the devices observed after one minute. The colors which formed were visually compared with one another and with a standard color chart, for relative intensity at one minute after immersion. The colors ranged from none (with the blank) to dark greenish-blue with the 0.139 mg/dL hemoglobin solution.

The results of this testing, summarized in the following table, show that test devices according to the present invention, tested in the two hemoglobin samples containing ascorbate both after being freshly prepared and after exposure to an elevated temperature of 50° C. for 10 days, elicited color responses to the presence of hemoglobin similar to the responses of the devices used to test the urine samples without ascorbate. The results from similar testing of the control devices which did not include Fe-HEDTA, showed the response of the control devices was virtually completely impaired by ascorbate in the sample. However, the devices produced according to this preferred embodiment of the invention evidenced an ability to easily detect hemoglobin at concentrations of 0.031 and 0.062 mg/dL, despite the presence of an ascorbate concentration of 50 mg/dL. Thus, the presence of the Fe-HEDTA appeared to dramatically curtail ascorbate interference.

inhibited by the ascorbate and, in fact, were able to respond, by the appearance of visually discernible color after one minute, to hemoglobin levels as low as 0.031 and 0.062 mg/dL.

In order to further demonstrate the advantages of the present invention, additional experimental testing similar to that aforedescribed was conducted with devices prepared as in Example XVII, i.e., containing Fe-HEDTA. However, rather than utilizing a visual technique, color formation was followed using a device known as the "Rapid Scanner". This device is a scanning reflectance spectrophotometer interfaced with a laboratory microcomputer. The instrument is used for the rapid measurement of reflectance spectra in the visual range. The computer enables the storage of spectral data and performs computations. Measurements of the performance of reagent strips in the Rapid Scanner have, for example, the following advantages over visual observation of the same strips:

1. The light source and conditions surrounding the sample remain fixed. In visual observations, the light source can vary, not only in wavelength, but also in relation to the location of the strip being observed.

| Urine sample Hemoglobin (mg/dl) | STABILITY PERFORMANCE OF TEST STRIP DEVICES OF THE INVENTION CONTAINING FE—HEDTA | | | |
|---|---|---|---|---|
| | Freshly-prepared strip devices at ambient temp.* | Strip devices stored at 50° C. for 10 days* | Strip devices stored at 50° C. for 28 days* | Freshly-prepared strip devices at ambient temp. without Fe—HEDTA* (Controls) |
| (no ascorbic acid) | | | | |
| 0 (Blank) | 10 | 10 | 10 | 10 |
| 0.015 | 20 | 20 | 15 | 22 |
| 0.031 | 25 | 25 | 22 | 30 |
| 0.062 | 32 | 30 | 30 | 35 |
| 0.139 | 45 | 40 | 38 | 40 |
| (50 mg/dl ascorbic acid) | | | | |
| 0.031 | 25 | 22 | 20 | 10 |
| 0.062 | 32 | 30 | 28 | 10 |

*The numbers in the table refer to test strip device performance as gauged by a standard color chart for existing occult blood strips. The chart is available from the Ames Division of Miles Laboratories, Inc. on the labelling for the occult blood test available as HEMASTIX ® On this color chart, a value of "10" is a negative reading, a "20" indicates trace hemoglobin or 0.015 mg/dL, and 30 and 40 correspond to 0.046 and 0.139 mg/dL hemoglobin, respectively.

The results from the foregoing table also demonstrate that there was little difference in reactivity between test devices of the present invention which had been freshly prepared and those which had been stored at 50° C. for 10 or 28 days. This result runs counter to the anticipated result: that interaction of ferric chelate and a hydroperoxide in same test device would cause a decrease in the device reactivity at a more rapid rate under heat stress than when stored at ambient temperature. This demonstrates the good stability and advantageous "shelf-life" of the composition and device of the invention. As seen from the data, there was little or no incompatibility evident between the organic hydroperoxide and Fe-HEDTA, between Fe-HEDTA and the indicator, or between these substances and other strip ingredients, even after prolonged storage at elevated temperatures. Moreover, metal chelate (Fe-HEDTA)-containing test devices, and devices similarly prepared without Fe-HEDTA, were substantially similar in sensitivity to the presence of hemoglobin in test solutions without ascorbate and showed a lack of "false positive" results, indicative of the outstanding compatibility of the reagents. However, while the devices prepared without Fe-HEDTA were virtually completely inhibited by the presence of ascorbate in the test solutions, the strips of the invention containing Fe-HEDTA were much less 2. The detector characteristics remain fixed. In visual observation, the detector (i.e., the eyes of the observer) can vary from person to person, and with the same person, from day to day.
3. The Rapid Scanner enables more precise quantitation of the data than does visual observation thereby permitting comparisons between results to be made in a more objective manner.

The Rapid Scanner instrument was constructed by the Ames Division of Miles Laboratories, Inc., Elkhart, Ind., from whom complete information with respect to structural and performance characteristics is obtainable. See also, M. A. Genshaw and R. W. Rogers, Anal. Chem., Vol. 53, pp. 1949–1952 (1981).

Tri-stimulus values from the Rapid Scanner were used to calculate color difference values ($\Delta E$) according to the convention contained within "Supplement No. 2 to Commission Internationale de L'Eclairage (Paris, France) Publication No. 15, Colorimetry, (E.-1.3.1) 1971." The data from this instrument are, therefore, recorded below in terms of $\Delta E$, or color difference units.

The test strip devices according to the invention which contained Fe-HEDTA were tested using the aforedescribed procedures for ability to detect hemoglobin concentrations of 0.031 mg/dL and 0.062 mg/dL. Some of the devices were tested in urine samples containing 50 mg/dL ascorbate, some in similar samples which did not contain ascorbate, some after being freshly prepared at ambient temperature, and some after storage at ambient temperature and 50° C., for 11 and 28 day periods.

The color difference units (ΔE) provided by the Rapid Scanner correspond to various hemoglobin levels. When the devices containing Fe-HEDTA were tested in urine samples containing 0.031 and 0.062 mg/dL hemoglobin, with and without ascorbate present, the results were as shown in the following series of tables:

| Urine Sample | | |
|---|---|---|
| Hemoglobin (mg/dL) | Ascorbic Acid (mg/dL) | Rapid Scanner Results (ΔE) Test Device |
| FRESHLY PREPARED DEVICES | | |
| 0.031 | 0 | 21.89 |
| 0.031 | 50 | 15.75 |
| 0.062 | 0 | 29.78 |
| 0.062 | 50 | 22.84 |
| DEVICES STORED AT AMBIENT TEMPERATURE FOR TWENTY-EIGHT (28) DAYS | | |
| 0.031 | 0 | 15.50 |
| 0.031 | 50 | 13.29 |
| 0.062 | 0 | 26.31 |
| 0.062 | 50 | 18.20 |
| DEVICES STORED AT 50° C. FOR ELEVEN (11) DAYS | | |
| 0.031 | 0 | 20.86 |
| 0.031 | 50 | 12.36 |
| 0.062 | 0 | 30.04 |
| 0.062 | 50 | 27.26 |
| DEVICES STORED AT 50° C. FOR TWENTY-EIGHT (28) DAYS | | |
| 0.031 | 0 | 10.31 |
| 0.031 | 50 | 7.78 |
| 0.062 | 0 | 20.86 |
| 0.062 | 50 | 16.38 |

The foregoing experiments present instrumental data which corroborate the visual data presented, supra. The data shows the stability of devices of the invention as well as a significant abatement of ascorbate interference in such devices even after prolonged storage and storage at elevated temperatures.

Additional visual testing was conducted on a set of test devices which had been prepared according to the invention as described in Example XVIII, supra, i.e., which contained Fe-EDTA. Following preparation of the devices, they were tested in urine samples conaining various concentrations of hemoglobin, and no hemoglobin, and in samples of two hemoglobin levels which contained 50 mg/dL ascorbate. Some of the devices were tested immediately after preparation, and some after storage in an oven at 50° C. for twenty-eight (28) days. The results of this testing are presented in the following table, wherein the numbers correspond to visual color values obtained by reference to the aforementioned HEMASTIX® standard color chart. All testing of these devices were carried out as previously described.

| STABILITY PERFORMANCE OF TEST STRIP DEVICES OF THE INVENTION CONTAINING Fe—EDTA | | |
|---|---|---|
| | Urine Sample | |
| Hemoglobin (mg/dL) | Freshly-prepared strip devices at ambient temp. | Strip devices stored at 50° C. for 28 days |
| (no ascorbic acid) | | |
| 0 | 10 | 10 |
| 0.015 | 12 | 11 |
| 0.031 | 20 | 15 |
| 0.062 | 30 | 22 |
| 0.139 | 35 | 30 |
| (50 mg/dL ascorbic acid) | | |
| 0.031 | 20 | 14 |
| 0.062 | 30 | 22 |

The results of these latter tests confirm the stability, lack of false positive results, and substantial ascorbate inhibition resistance of devices produced according to this further embodiment of the invention.

It is apparent that many modifications and variations from the preferred embodiments of the invention specifically disclosed may be possible without departing from the spirit and scope thereof. Accordingly, it is intended that any limitations be imposed imposed upon the invention only as set forth in the following claims.

What is claimed is:

1. In a composition for detecting the presence of a peroxidatively active substance in a test sample, the composition comprising an organic hydroperoxide and an indicator capable of providing a detectable response in the presence of the peroxidatively active substance and peroxide, the improvement wherein the composition additionally comprises a metal chelate of a polycarboxyalkylamine derivative having a general formula:

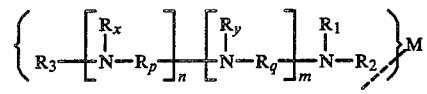

where:
(a) $R_1$ is hydrogen or straight or branched chain alkyl alcohol or alkyl carboxylic acid radicals having from 2 to 3 carbon atoms; $R_2$, $R_3$, $R_x$ and $R_y$, same or different, are straight or branched chain alkyl alcohol or alkyl carboxylic acid radicals having from 2 to 3 carbon atoms; where at least two of $R_1$, $R_2$, $R_3$, $R_x$ or $R_y$ are alkyl carboxylic acid radicals so defined;
(b) $R_p$ and $R_q$, same or different, are straight or branched chain alkylene radicals having from 1 to 3 carbon atoms or divalent 1,2-cycloaliphatic radicals having from 6 to 9 carbon atoms;
(c) n is an integer having a value of from 0 to 1; m is an integer having a value of from 0 to 2; where if m is greater than 0, repeated $R_p$ and repeated $R_q$ radicals may be the same or different; and
(d) M is $Fe^{+3}$.

2. The composition of claim 1 in which
(a) m is 0; and
(b) $R_p$ is an ethylene radical.

3. The composition of claim 1 in which at least two of $R_1$, $R_2$, $R_3$, $R_x$ and $R_y$ are the alkyl carboxylic acid radical, —$CH_2COOH$.

4. The composition of claim 1 in which the indicator is benzidine; o-tolidine; a 3,3',5,5'-tetra(lower alkyl)benzidine; 2,7-diaminofluorene; or mixtures thereof.

5. The composition of claim 1 in which the metal chelate is selected from the group consisting of ferric chelates of N-(2-hydroxyethyl)ethylenediaminetriacetic acid, ethylenediaminetetraacetic acid, cyclohexylenediaminetetraacetic acid, nitrilotriacetic acid, iminodiacetic acid, α-ethylenediaminediaceticdipropionic acid, β-ethylenediaminediaceticdipropionic acid, hydroxylethylaminodiacetic acid and mixtures thereof.

6. The composition of claim 1 in which the metal chelate is a ferric chelate of N-(2-hydroxyethyl)-ethylenediaminetriacetic acid.

7. The composition of claim 1 in which the metal chelate is a ferric chelate of ethylenediaminetetraacetic acid.

8. The composition of claim 1 in which the organic hydroperoxide is selected from the group consisting of cumene hydroperoxide; t-butyl hydroperoxide, diisopropylbenzene hydroperoxide, 2,5-dimethylhexane-2,5-dihydroperoxide; paramenthane hydroperoxide; and mixtures thereof.

9. The composition of claim 1 in which organic hydroperoxide is cumene hydroperoxide and the indicator is 3,3',5,5'-tetramethylbenzidine.

10. The composition of claim 1 in which the indicator is 3,3',5,5'-tetramethylbenzidine, the metal chelate is a ferric chelate of N-(2-hydroxyethyl)-ethylenediaminetriacetic acid and the organic hydroperoxide is cumene hydroperoxide.

11. A test means for determining the presence of a peroxidatively active substance in a test sample, comprising a carrier matrix incorporated with the composition of claim 1.

12. A test means for determining the presence of a peroxidatively active substance in a test sample, comprising a carrier matrix incorporated with the composition of any of claims 2 to 10.

13. A method for preparing a test means for determining the presence of a peroxidatively active substance in a test sample, wherein the test means is resistant to interfering affects of ascorbate which may be present in the sample, which method comprises the steps of:

(a) preparing a first reagent solution including an organic hydroperoxide, and a metal chelate of an polycarboxyalkylamine derivative having the general formula:

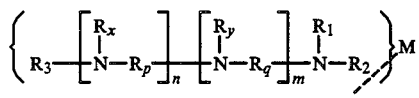

where:
(i) $R_1$ is hydrogen or straight or branched chain alkyl alcohol or alkyl carboxylic acid radicals having from 2 to 3 carbon atoms; $R_2$, $R_3$, $R_x$ and $R_y$, same or different, are straight or branched chain alkyl alcohol or alkyl carboxylic acid radicals having from 2 to 3 carbon atoms; where at least two of $R_1$, $R_2$, $R_3$, $R_x$ or $R_y$ are alkyl carboxylic acid radicals so defined;

(ii) $R_p$ and $R_q$, same of different, are straight or branched chain alkylene radicals having from 1 to 3 carbon atoms or divalent 1,2-cycloaliphatic radicals having from 6 to 9 carbon atoms;

(iii) n is an integer having a value of from 0 to 1; m is an integer having a value of from 0 to 2; where if m is greater than 0, repeated $R_p$ and repeated $R_q$ radicals may be the same or different; and (iv) M is $Fe^{+3}$;

(b) incorporating the first reagent solution with a carrier matrix by wetting the matrix with the first solution;

(c) drying the wetted matrix to leave a residue of the metal chelate and the hydroperoxide;

(d) preparing a second reagent solution including an indicator and a solvent, the indicator being capable of providing a detectable response in the presence of a peroxide and the peroxidatively active substance;

(e) incorporating the second reagent solution with the dried carrier matrix by wetting the matrix with the second reagent solution; and (f) drying the matrix to leave a combined residue including the metal chelate, the hydroperoxide and the indicator.

14. The method of claim 13 in which
(a) m is 0; and
(b) $R_p$ is an ethylene radical.

15. The method of claim 13 in which at least two of $R_1$, $R_2$, $R_3$, $R_x$ and $R_y$ are the alkyl carboxylic acid radical, —$CH_2COOH$.

16. The method of claim 13 in which the indicator is benzidine; o-tolidine; a 3,3',5,5'-tetra(lower alkyl)benzidine; 2,7-diaminofluorene; or mixtures thereof.

17. The method of claim 13 in which the metal chelate is selected from the group consisting of ferric chelates of N-(2-hydroxyethyl)ethylenediaminetriacetic acid, ethylenediaminetetraacetic acid, cyclohextlenediaminetetraacetic acid, nitrilotriacetic acid, iminodiacetic acid, α-ethylenediaminediaceticdipropionic acid, β-ethylenediaminediaceticdipropionic acid, hydroxylethylaminodiacetic acid and mixtures thereof.

18. The method of claim 13 in which the metal chelate is a ferric chelate of N-(2-hydroxyethyl)-ethylenediaminetriacetic acid.

19. The method of claim 13 in which the metal chelate is a ferric chelate of ethylenediaminetetraacetic acid.

20. The method of claim 13 in which the organic hydroperoxide is selected from the group consisting of cumene hydroperoxide; t-butyl hydroperoxide, diisopropylbenzene hydroperoxide, 2,5-dimethylhexane-2,5-dihydroperoxide; paramenthane hydroperoxide; and mixtures thereof.

21. The method of claim 13 in which organic hydroperoxide is cumene hydroperoxide and the indicator is 3,3',5,5'-tetramethylbenzidine.

22. The method of claim 13 in which the indicator is 3,3',5,5'-tetramethylbenzidine, the metal chelate is a ferric chelate of N-(2-hydroxyethyl)-ethylenediaminetriacetic acid and the hydroperoxide is cumene hydroperoxide.

23. A method for determining the presence of a peroxidatively active substance in a test sample, comprising the steps of contacting the sample with the test means of claim 11 and observing a detectable response.

* * * * *